(12) United States Patent
Dauga et al.

(10) Patent No.: US 7,648,364 B2
(45) Date of Patent: Jan. 19, 2010

(54) SYSTEM AND METHOD FOR APPLYING A COSMETIC SUBSTANCE

(75) Inventors: Christophe Dauga, Levallois-Perret (FR); Francis Xavier Quinn, Paris (FR)

(73) Assignee: L'Oreal, Paris (FR)

( * ) Notice: Subject to any disclaimer, the term of this patent is extended or adjusted under 35 U.S.C. 154(b) by 311 days.

(21) Appl. No.: 10/069,402

(22) PCT Filed: Jun. 26, 2001

(86) PCT No.: PCT/FR01/02021

§ 371 (c)(1),
(2), (4) Date: Dec. 9, 2002

(87) PCT Pub. No.: WO02/01499

PCT Pub. Date: Jan. 3, 2002

(65) Prior Publication Data

US 2004/0078278 A1 Apr. 22, 2004

(30) Foreign Application Priority Data

Jun. 26, 2000 (FR) .................................. 00 08175

(51) Int. Cl.
*G09B 19/00* (2006.01)
(52) U.S. Cl. ........................................ 434/100; 601/17
(58) Field of Classification Search ................. 434/100; 606/186, 9; 601/17
See application file for complete search history.

(56) References Cited

U.S. PATENT DOCUMENTS

| 4,160,271 | A | 7/1979 | Grayson et al. |
| 5,495,338 | A | 2/1996 | Gouriou |
| 5,836,872 | A | 11/1998 | Kenet et al. |
| 6,199,557 | B1 * | 3/2001 | Laughlin ..................... 132/200 |
| 6,295,737 | B2 * | 10/2001 | Patton et al. .................. 33/18.1 |
| 6,575,751 | B1 * | 6/2003 | Lehmann et al. ............. 433/223 |
| 2003/1006081 | * | 3/2003 | Syrowicz et al. ............... 606/9 |

FOREIGN PATENT DOCUMENTS

| DE | 195 26 650 A | 1/1997 |
| EP | 0 523 961 A1 | 1/1993 |
| FR | 2561515 | 9/1985 |

OTHER PUBLICATIONS

XP001247359; "A Robotic Make-over: The Handy-One Now Manipulates Make-up Brushes."
Linn et al., "Treatment of Melasma Using Kojic Acid in a Gel Containing Hydroquinone and Glycolic Acid," Dermatol Surg., 1999, 25(4):282-284.
XP001247359; "A Robotic Make-over: The Handy-One Now Manipulates Make-up Brushes.", p. 1.

\* cited by examiner

*Primary Examiner*—Cameron Saadat
(74) *Attorney, Agent, or Firm*—Pillsbury Winthrop Shaw Pittman LLP

(57) ABSTRACT

The invention concerns a make-up or coloring method comprising steps which consist in imaging at least one part of the human body to be treated, analysing local characteristics of said part, and applying treatment products of said part based on said local characteristics.

24 Claims, 4 Drawing Sheets

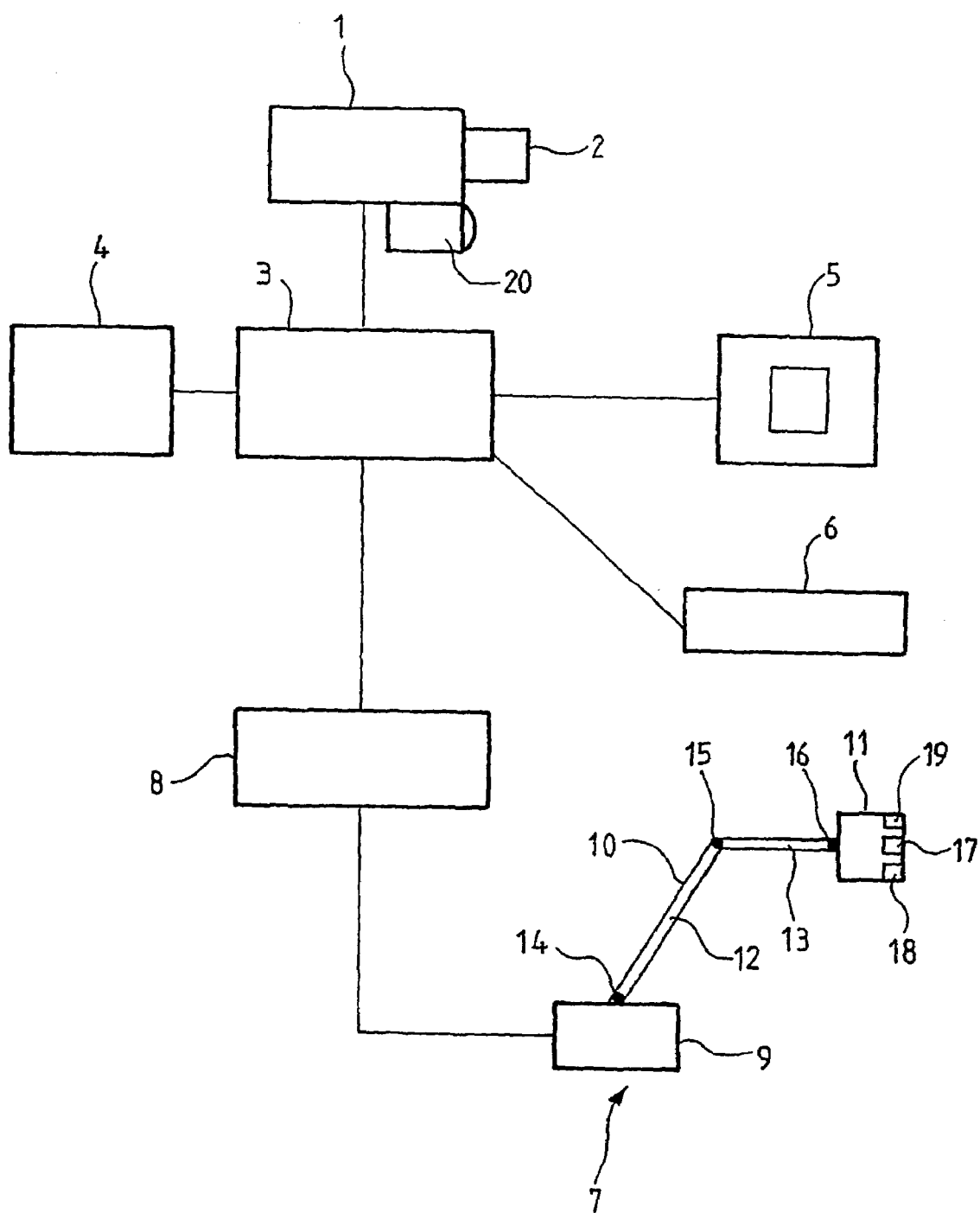
FIG_1

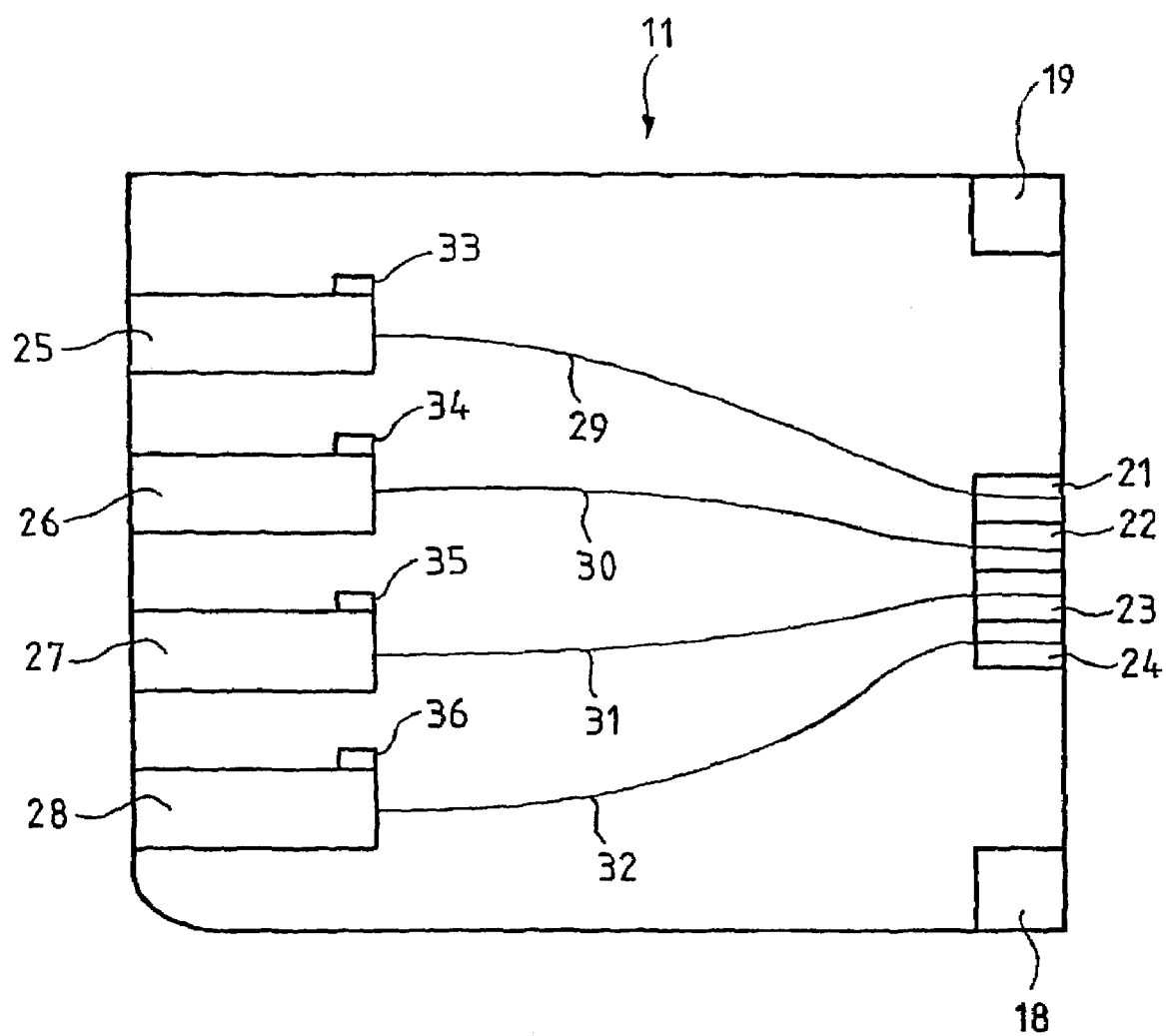
FIG_2

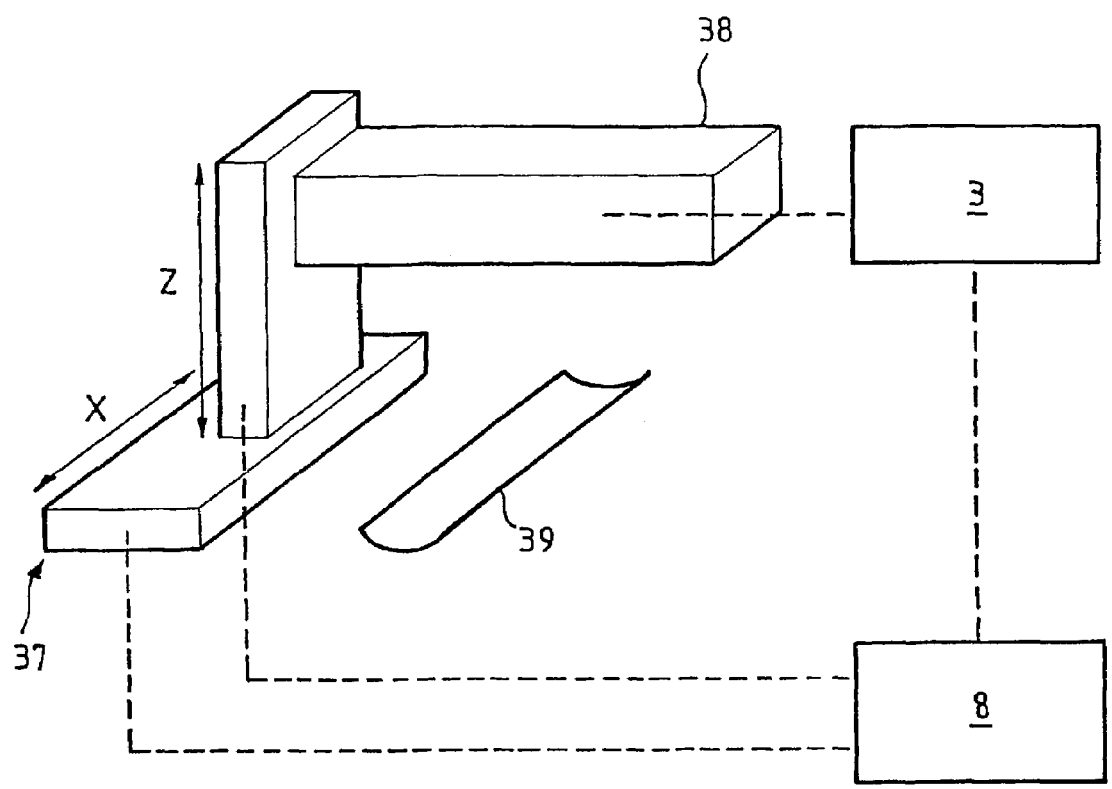
FIG_3

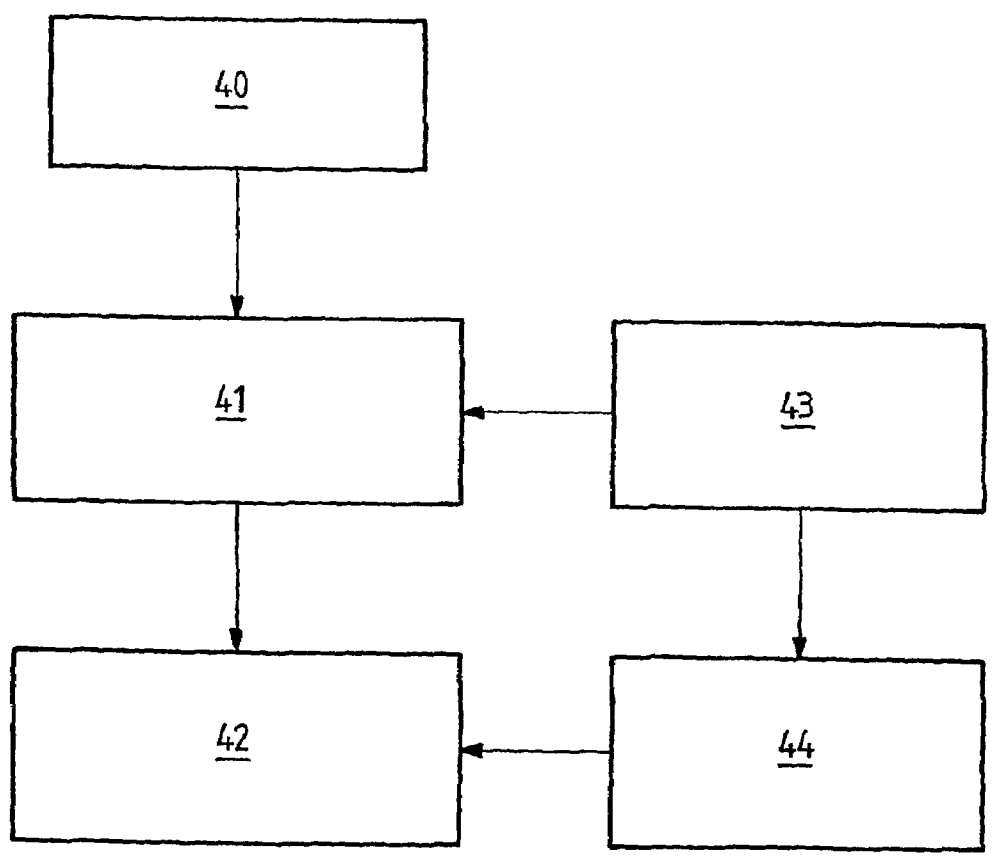
FIG_4

SYSTEM AND METHOD FOR APPLYING A COSMETIC SUBSTANCE

The present invention relates to the treatment, especially the cosmetic making up, dyeing or care, of some or all of the human body.

The technique of tattooing has been known since ancient times and consists in indelibly inserting dyeing substances under the epidermis.

Tattooing makes it possible to obtain a color design of very high quality, but requires delicate intervention, especially in terms of health risk because of the incision of the skin. As a result, many people abandon the idea of being tattooed because of the indelibility and the surgical aspect of the operation.

Makeup products which temporarily offer some covering effect and can substantially alter the appearance of the part of the body which they cover are also known. Document U.S. Pat. No. 5,785,960 describes an apparatus for manufacturing a composition for dyeing the skin using a reading of the skin color.

Makeup products are easy to apply, but they do not stay on for more than a few hours, particularly in hot and/or humid weather.

Moreover, makeup products seek to imitate the appearance of a normal skin and do not offer any freedom of design.

Small stamping pads for applying a design onto the skin by transfer printing have recently appeared. The durability of the design on the skin is of the order of a few days. However, no freedom of design is offered.

The user reproduces only the design present on the stamping pad.

The present invention proposes to overcome the drawbacks mentioned hereinabove.

The present invention proposes a process for treatment, especially for makeup or for temporary dyeing, without incision of the skin, capable of taking account of the local characteristics of the skin and offering a complete freedom of design.

The present invention proposes a device for implementing the process hereinabove. The device comprises a means of positioning said part, a means of taking images, a means of analyzing images in order to obtain the local characteristics of said part, and a means of applying treatment products over said part according to said local characteristics.

The process for treatment, especially for care, for makeup or for dyeing, according to one aspect of the invention, comprises steps of taking at least one image of at least one part of the body, especially a human body, to be treated, of analyzing local characteristics of said part from the image, and of applying, by means of a machine, suitable treatment products over said part according to said local characteristics, said machine being controlled by at least one signal generated on the basis of the analysis of said local characteristics.

Advantageously, the process comprises steps of recognizing the desired visual characteristics and of applying treatment products, especially makeup or dyeing products, over a part to be treated, especially to be made up, according to said desired characteristics.

Advantageously, the process comprises steps of defining particular areas of said part and of applying makeup or dyeing products successively over said particular areas.

In one embodiment of the invention, the process comprises a step of storing, for a given person, the products used and the visual characteristics obtained.

Advantageously, the local characteristics obtained immediately after applying the treatment products are monitored.

The monitoring may be carried out by feedback or automatic control, with real-time correction of the makeup operation or of the treatment, if necessary.

In one embodiment of the invention, the application of treatment products is carried out by a moving application head which follows the relief of the part while remaining a short distance away or while being in contact. The head may comprise a powder puff, a roll or a coarse or fine brush, usually used in cosmetics.

In one embodiment of the invention, the distance between the moving application head and said part is monitored in real time.

In one embodiment of the invention, the monitoring of the local characteristics obtained immediately after the application of the products is carried out using the moving application head.

Several treatment products, for example 2, 3 or 4, especially makeup and/or care products, can be applied simultaneously by the moving application head.

In one embodiment of the invention, the moving application head is supported by an arm which is articulated in order to be capable of following the relief of said part.

In one embodiment of the invention, the moving application head comprises at least one nozzle capable of spraying a treatment product, said head being of the piezoelectric, pneumatic, electrospray, thermospray or aerosol type.

Advantageously, the flow rate of each product can be varied according to the coordinates of the site onto which said product is being applied. A step of recognizing said part may be implemented in order to determine to which organ said part belongs, for example the arm, the hand, the scalp, the face and its parts such as the eye, eyelid, pupil, cheek, eyelash, eyebrow, lip, forehead and nose.

A two- or three-dimensional reconstruction of said part may be provided in order to obtain a two- or three-dimensional, preferably a three-dimensional representation. The three-dimensional representation is produced especially from at least two images.

In one embodiment of the invention, the treatment products are applied by airbrushing, by transfer printing, by tattooing or by a wipe impregnated with the product to be applied.

In one embodiment of the invention, at least one digital image of said human body part to be treated is taken. A digital camera, for example a CCD camera, may be used to this end.

In another embodiment of the invention, the digital image or images of said human body part to be treated is/are digitized. An analog/digital conversion means may be provided to this end.

In one embodiment of the invention, the image taking and application steps are carried out in a first zone, and the analysis step is carried out in a second zone distinct from the first zone, with communication between said zones by means of a telecommunications network, of the Internet type.

In another embodiment of the invention, the image taking step is carried out in a first zone, the analysis step is carried out in a second zone distinct from the first zone, and the application step is carried out in a third zone distinct from the first and second zones, with communication between said zones by means of a telecommunications network, of the Internet type.

In one embodiment of the invention, a signal intended to control an application machine is generated.

In one embodiment of the invention, said signal is used to control said application machine.

The positioning means may be a cast or a chin strap intended to immobilize the part to be treated (arm or head).

The image analysis means may be software which, in principle, is aware of the position and the shape of the part to be treated (for example the lips), especially software which processes the image by regional growth.

The device may be provided with rollers which are motorized or non-motorized for contact with the human body and relative displacement with respect to the latter, the axes of the rollers being fixed with respect to the application means in order to maintain a determined distance between the application means and the human body.

The device may comprise a support for the human body part having to receive the treatment product or products.

A light source may be combined with the image taking means.

The application means may be supported by an articulated arm and may comprise a nozzle, for example of the piezoelectric type.

The device may comprise means for controlling the position of the application head with respect to the part of the area to be treated.

The device may comprise a means for automatically controlling the total amount and the respective amounts of each composition and of each ingredient according to the desired characteristics, especially with feedback.

Thus, the invention offers the advantages of freedom of design of conventional tattooing, the ease of use of a makeup operation and an average durability which may be readily controlled according to the wishes of the user, from a few hours to about 20 days. The fact that the local characteristics of said part are taken into account further increases the visual quality of the drawing obtained, especially to play with three-dimensional or perspective or even optical effects, enabling some skin imperfections to be made invisible.

The term "part of the body, especially the human body" refers herein to the skin, for example of the face, of a limb, etc., the scalp, mucus membranes, semi-mucus membranes, keratinous fibers, for example the eyelashes, eyebrows, head hair, the nails and body hair.

The term "image" refers herein a two-dimensional representation of the appearance of an object composed of unit elements to be analyzed, the analysis zone may be limited to a single element (a pixel, for example).

The present invention will be better understood on studying the detailed description of a number of embodiments taken by way of nonlimiting examples and illustrated by the appended drawings, in which:

FIG. 1 is a schematic view of a device, according to one embodiment of the invention;

FIG. 2 is a detail view of FIG. 1;

FIG. 3 is a schematic view according to another embodiment of the invention;

FIG. 4 is a diagram showing the image acquisition steps in a device according to the invention;

As can be seen in FIG. 1, the makeup or dyeing system comprises at least one camera 1 equipped with an objective 2, a central processing unit 3 equipped with a memory 4, a screen 5 and a keyboard 6, and an applicator 7 provided with control means 8. The video camera 1 may be of the CCD type. Alternatively, the camera may be of the conventional type, an analog/digital conversion means then being provided. Communications between these various elements may be provided by a connection of the RS 232 type. The memory 4 and the screen 5 may be integral with the central processing unit or placed in separate cases. The presence of the keyboard 6 is optional and may be replaced by a touch screen 5 making it possible to carry out commands. A mouse or a device of the same type may also be provided.

The applicator 7 comprises a case 9 which may be fixed to the floor or to any suitable support, an articulated assembly 10 fixed at one end to the case 9 and supporting at the opposite end a product application head 11.

The articulated assembly 10 comprises two arms 12 and 13. The arm 12 is mounted so as to pivot on the case 9 by means of an articulation 14. The arm 13 is mounted so as to pivot on the arm 12 by an articulation 15 and the head 11 is mounted so as to pivot on the arm 13 by means of an articulation 16. The articulations 14, 15 and 16 are motorized or provided with actuators for moving the head 11 with respect to the case 9 along several axes, preferably perpendicular to each other. Optionally, the arms 12 and 13 may be telescopic, for example by means of an electric cylinder. If it is desired for the head 11 to carry out more complex movements, more than three articulations may be provided so that they give said head 11 a larger number of degrees of freedom.

A light source 20 may be attached to the camera 1 in order to improve the lighting and therefore the quality of the images obtained. The light source 20 will be active at least in visible light and may be of the light-emitting diode, xenon arc, halogen, etc., type.

The application head 11 comprises a row of spraying nozzles 17 fed with treatment products from one or more reservoirs (not shown), for example placed in the case 9, and two distance sensors 18 and 19 capable of measuring the distance between the application head 11 and the surface on which the treatment product is to be applied. The detectors 18 and 19 may each include a laser diode emitting a laser beam adjusted to cross the other laser beam emitted by the other diode at the desired distance between the head 11 and the surface which is to receive the treatment product, such that a difference with respect to this desired distance can be readily detected. The nozzles 17 may be of the inkjet type with a piezoelectric crystal or an electrostatic means.

Inkjet printing is a contact-free process. The ink is emitted from nozzles. Liquid inks of various colors spurt onto the surface to be treated in order to form an image. The application head 11 sweeps over said surface in parallel strips. In order to increase the printing speed, the application head 11 simultaneously prints in one pass a row of pixels by means of the row of nozzles 17. The inkjet technique is generally either thermal or electrostatic or even piezoelectric.

In the present application, the piezoelectric technique, in which a piezoelectric crystal is placed in the bottom of a product reservoir close to a nozzle, is preferably used. When a current is applied to the piezoelectric crystal, it becomes deformed, which creates a force sufficient to eject a droplet of product. The product does not need to be heated and the droplets may be of very small size. In order to obtain color designs, cyan, magenta and yellow color product cartridges will be provided. Preferably, a black color cartridge will also be provided in order to obtain a good quality black. Two additional cartridges, light cyan and light magenta, may also be provided for finer designs.

Of course, product characteristics other than the color characteristics will be adapted to that part of the human body intended to receive them: skin, nails, hair, etc. Moreover, cartridges of care product and/or of makeup product will also be provided.

The system operates as follows. A person wishing to treat part of his body, for example the face, the hand, the hair, etc., is installed in the field of vision of the camera 1 for one or more views to be taken. Specifically, the production of a three-dimensional image of the part of the human body which is a preferred variant, requires at least two views to be taken from different angles by means of at least two fixed cameras or by means of one moving camera. The image files obtained on taking these views are transferred from the camera 1 to the central processing unit 3 which performs processing generally known as reconstruction and allowing a three-dimensional image to be obtained, which is then transferred to the memory 4. To improve the quality of the three-dimensional image, optional processing treatments may be carried out by the central processing unit, for example to correct geometrical defects associated with the perception of the relief. The three-dimensional image obtained and stored in the memory 4 may be displayed on the screen 5. In the case of a three-dimensional image, it is not essential for the central processing unit 3 to perform such processing. Design software stored in the memory 4 allows the user, or an operator who may assist him, to simulate on the screen 5 various possible makeup operations or dyeings according to preexisting designs stored in the memory 4, or designs provided by the user on a digital medium such as a floppy disk or a CD ROM capable of being read by a suitable reader (not shown) connected to the central processing unit 3. Retouching may be performed by means of the keyboard 6 or the screen 5 if the latter is of the touch-type, until the effect desired by the user is obtained on the screen 5. The design may also be entirely composed by the user or by the operator. Design software such as PHOTOSHOP® from Adobe or PAINTBRUSH® from Microsoft may be used.

At the same time that this is choice is made by the user, the central processing unit performs an analysis of the characteristics of the surface to be made up or colored from the two- or three-dimensional image, so as to determine the topological characteristics of said surface, in order to determine whether an application of a treatment product is necessary prior to the application of a makeup or dyeing product, for example in the case of a dry skin or even in the case of a wrinkled skin. The two-dimensional image is suitable for dry skin or for nonuniform colors (pigmentation mark or scar). For wrinkled skins, the three-dimensional image is preferred.

The central processing unit 3 also performs processing allowing various parts of the human body to be recognized, especially to differentiate hair from skin, to recognize the fingers and the nails of a hand and to recognize the various parts of the face, especially the lips, the eyebrows, the cheeks and more generally any part requiring the application of a specific treatment, makeup or dyeing product, for example by means of segmentation-recognition software.

At the end of these steps, the central processing unit 3 prepares a signal for controlling the applicator 7 and sends it to the control means 8. The control means 8 control the following operations according to the control signal received from the central processing unit 3.

The application head 11 is brought into the field of vision of the camera 1 and placed close to the surface which is to be made up or dyed, so that the row of nozzles 17 is at the desired spraying distance, which is verified using the sensors 18 and 19. Of course the part of the user's body which is to be treated will be properly immobilized for the duration of the treatment. The head-surface distance is dynamically controlled in real time by the control means 8.

In the case of applying makeup, a first passage of the head 11 may allow a care product to be deposited and a second passage will allow the makeup product itself to be deposited.

Advantageously, it is possible to provide for a third passage of the head 11. The second passage then allows a color product to be deposited and the third passage allows a matting agent to be deposited.

In the case of a pigmentation mark detected by the camera 1 and identified by the central processing unit 3, the treatment product could be or could comprise a covering product making it possible to give the pigmentation mark the same appearance as the rest of the skin.

By way of a variant, it is possible to envisage simultaneously depositing two or more products so as to accelerate the process. To this end, several rows of nozzles 17 arranged in a matrix may be provided allowing different products to be applied simultaneously but in sites which are slightly offset. In the event of scars being present, they may be camouflaged by applying dye with optical illusion patterns, making it possible to give an illusion of relief. The central processing unit 3 will perform a colorimetric analysis of the image perceived by the camera 1, so as to determine the local shade of the part having to be treated.

A dyeing product, for example an ink, may be applied in order to obtain the image selected by the user on the screen 5. A step of applying a varnish and/or a product intended to prevent desquamation and enabling the staying power of the dyeing to be prolonged may then be included. Of course, an ink and possibly a varnish which can be removed without damaging the skin, for example by an organic solvent, by water or by a surfactant product, will be chosen.

The care products used prior to the makeup or dyeing product may also be made by mixing a dye and a care product at low dose such as hydroquinone, kojic acid or arbutin. It is also possible to add to the dyeing or makeup product a self-tanning agent, for example dihydroxyacetone or even a substrate and enzyme assembly reacting in situ on the skin during the application, it being possible for the substrate to be a polymer of the polyphenol family.

In the case of dyeing or making up a skull, the hair of which is cut extremely short, products intended for the skin will be used to produce the pattern desired by the user, such as stripes, degradations, streaks, etc.

The spraying nozzles 17 may be of the piezoelectric spraying type, allowing a wide variety of treatment or pigment products to be used. The product is forced through the nozzle which is of small diameter and made to vibrate at high frequency by a piezoelectric crystal placed in the head 11. The product in liquid form then splits into fine droplets which are expelled by the nozzle. At the outlet, the droplets may be diverted by any known means, such as by means of deflection electrodes, allowing multidiverted continuous jet printing.

The entire surface to be made up or dyed is crossed by the head 11 with real time measurement of the distance by means of the sensors 18 and 19 for maintaining the distance required by the type of nozzle that is used, thus allowing accurate monitoring of the relief and a high-quality application.

FIG. 2 illustrates in more detail the moving head 11. The set of nozzles 17 comprises four nozzles 21, 22, 23 and 24, four removable cartridges 25, 26, 27 and 28, each one containing a product that it is desired to apply and being connected via a tube 29, 30, 31, 32 to the corresponding nozzle 21, 22, 23, 24. By way of example, the cartridges 25 to 28 may contain:

each a base dyeing composition;
    each a dyeing composition derived from a mixture;
    one a covering product of the foundation type, the others different dyeing compositions, etc.

The moving head 11 comprises a means of identifying cartridges 25 to 28, for example in the form of four sensors 33 to 36, each one dedicated to a cartridge 25 to 28 and capable of recognizing the contents of the cartridge, especially by reading a mechanical, optical, magnetic, etc. code.

Product pumping means are also provided to transfer a product from a cartridge 25, 26, 27, 28 to the corresponding nozzle 21, 22, 23, 24. The moving head 11 may comprise a means of monitoring the amount of product present in each cartridge 25, 26, 27, 28, for example in the form of a sensor dedicated to measuring the mass of a cartridge 25, 26, 27, 28 and allowing the product level to be estimated, or of a sensor dedicated to measuring the flow rate of a pumping means, or else a sensor dedicated to measuring the electric current consumed by a pumping means, the current decreasing when a cartridge is empty and the pumping means no longer delivers product. An empty cartridge may be indicated by displaying an "empty cartridge" message on the screen 5 and/or by emitting a sound signal. Alternatively, the screen 5 may comprise a zone dedicated to displaying the level of product in each cartridge.

The moving head 11 may comprise a means for maintaining the temperature if the nature of the products, especially their viscosity, requires it, for example between 20 and 27° C., better still between 22 and 24° C. The maintenance of a relatively constant temperature avoids a dispersion of flow from the nozzles due to a variation in viscosity.

Thus, after selecting the desired visual characteristics, the software stored in the memory 4 and implemented by the central processing unit 3 verifies that the cartridges present in the head 11 are suitable for the desired visual characteristics. If such is not the case, a warning message is displayed on the screen 5.

Verification is carried out from the signals emitted by the sensors 33 to 35 and received by the central processing unit 3, for example by a wire connection passing through the case 9.

After the operator has made available, if necessary, suitable cartridges in the head 11, a corresponding message may be displayed on the screen 5.

In other embodiments, the head 11 may comprise an application means such as an airbrush or a means of application by transfer printing, by tattooing or by a wipe impregnated with the product to be applied.

The software calculates the instantaneous amounts of each product for each elementary area of the part to be treated according to the characteristics of said elementary area. In other words, for an elementary area of coordinates (x, y) or (x, y, z), the software calculates the partial elementary amounts $Q_{25}$, $Q_{26}$, $Q_{27}$ and $Q_{28}$ of product from cartridges 25, 26, 27 and 28 according to the type of each product, the characteristics of the elementary area and the result to be obtained which may be defined by color and brightness variables.

The software also determines the order of application of the products which may be successive over the same area or juxtaposed over neighboring areas. In some cases, only one product will be applied and only one cartridge will be used even if others remain in place on the head 11.

In order to have a direct correlation between the visible characteristics of the skin and the two- or three-dimensional mathematical information, the software may use, for example, an optical measurement process which uses a combination of Gray code and phase shift techniques. With this process, it is possible to determine with great accuracy the absolute spatial coordinates of all the object points in the field covered by the image.

In the Gray code method, the fringes are projected successively with a rectangular luminosity modulation and a different number of lines. The number of lines is doubled at each projection process, thus unambiguously defining the order of the lines for each image point. In the phase shift method, only one fringe is projected several times with a sinusoidal luminosity modulation and a different phase relationship. This also allows an exact three-dimensional reconstruction of the surface for which each image point is defined independently of its neighbors, an automatic control of the measuring quality.

The resolution in the vertical Z direction, typically with 0.2% of the measuring field, leads to an effective resolution of 4 μm in Z. Depending on the type of CCD camera used, a resolution of 45 μm can be reached in the horizontal X and Y direction. The image analysis sequence with analysis of the corresponding coordinates may be performed in less than a second (typically 500-800 ms).

The three-dimensional coordinates of the area observed by the camera 1 serve to position the head 11 at a suitable distance (typically 1 cm) from the skin. This is performed by controlling a Z-translation table by means of the central processing unit 3.

The image acquired by the camera 1 for calculating the three-dimensional coordinates of the area observed also makes it possible to measure the color of the skin. To do this, the camera 1 is colorimetrically calibrated as is done for a scanner using an image of a calibration test card and calibration software, for example Profile maker from Logo. To overcome skin brightness phenomenon, polarizers in the crossed position are used, which are placed on the projector 20 and in front of the objective of the camera. This calibration procedure makes it possible to obtain correspondence of the image acquired with the colorimetric system and independent of the camera. The image makes it possible to have the color on each pixel and thus at each point of the area observed.

The positioning system 37, illustrated in FIG. 3, consists of two translation tables with stepper motors secured to each other, driven via a control unit. These tables allow the displacement of the distribution head 38 in Z (distance to the application area) and in X (translation along the application area).

The distance from the distribution head 38 to the area to be treated may vary between 20 μm and 10 cm, preferably between 100 μm and 5 cm, and preferably, between 250 μm and 1 cm.

The area of the body to be treated is kept in place using a suitable device. Mention is made, for example, of a cast 39 for the arm and of a chin strap (not shown) for the head.

Design software supporting the screen and printing colorimetric calibrations (of the type Photoshop V5.02 from Adobe) makes it possible to select from an image database the type of makeup to be applied to the area and to visualize the result after application. The image acquired by the calibrated camera allows the exact restoration of the colors of the area.

By means of the image modification software, it is possible to selectively correct a defect in the area to be treated (example: depigmented area). This area is encircled using the mouse and may be corrected using the same color as the surrounding skin.

The colors are obtained by mixing together the four colors: cyan, magenta, yellow, black. The head is colorimetrically calibrated (ICC profile) so as to perfectly restore the colors of the makeup selected and viewed on the screen.

In a preferred embodiment of the invention, the position of the distribution head 38 with respect to the skin may be dynamically controlled by means of a telemetry system. For example, by using a contact-free distance sensor operating on the principle of triangulation. The sensor has a measuring dynamic of plus or minus 1 cm with a precision less than 10 μm and a working distance of 6.5 cm, for example of the BULLIER INTERNATIONAL type, Reference M5L/20. The signal from the sensor is digital and is connected to the central processing unit. The automatic control of the position of the distribution head makes it possible to compensate for small movements of the area to be treated. The automatic control is carried out by the central processing unit during printing of the selected design.

By virtue of the invention, a makeup operation, a dyeing or a care treatment adapted to the user's wishes may be provided. The term "makeup operation" herein means the application of product taking into account the colorimetric and topological characteristics of the skin, and the term "dyeing" means the application of a covering product completely camouflaging the original shade of the skin. The system also applies to hair coloring. Patterns of different colors and of different shapes may be produced thereon by means of this automatic treatment machine.

The presence of several cartridges makes it possible to prevent the formation of a mixture of products prior to the application. On the contrary, each product is applied directly. Thus the use of an excessive amount of products is avoided, the mixture of which is specific to one person or to one localized site of a person and may not be used elsewhere.

FIG. 4 illustrates the various steps of the image acquisition process, especially in the case of two identical cameras looking at an object from two different optical paths. The two images, called a left image and a right image, are acquired at the same time, since the two cameras are synchronized. The view-taking is immediate, which eliminates any problems of user movement. The working volume is limited by the size of the vertical and horizontal fields of the cameras and by the depth of field of the objectives. The two views show disparities which may be quantified, which make it possible to return to the topography of the observed surface. The topography of the observed object is calculated in step 40 by acquiring the left and right images, in step 41 by calculating the optical geometry with interpolation and correcting the images provided by the central processing unit 3 of FIG. 3, in step 42 of calculating the disparities between the left and right images and by calculating the topography of the surface.

By way of example, in step 43, the calibration data are obtained using a test card which is moved in the working volume of the two cameras, the calibration being performed on one hundred points per plane over several planes separated by a step, for example of a few millimeters depending on the object to be measured. Parameters extrinsic to the cameras relating to the positions and orientations with respect to the calibration reference point, and parameters intrinsic to the cameras (optical characteristics) linked to the associated distortion and pinhole model, are extracted therefrom. This calibration is done once only and defines the geometry of the two cameras. Calculation of the disparities between the cameras is carried out on two different scales. Next, the correlation minimum between the two views is searched for at the two scales described. The position of this minimum is interpolated parabolically, which gives sufficient accuracy with an error of less than one pixel. The height of the point selected is inversely proportional to the calculated position of the minimum. The calibration data calculated in step 43 are supplied during step 41 for calculating the optical geometry and during a step 44 for calculating new parameters of the cameras, which are supplied to the central processing unit during step 42 of calculating the topography of the surface.

The treatment product which may be applied within the scope of the present invention may be of any cosmetically acceptable nature.

It may be a care, makeup or dyeing product, which may be applied to the skin of the body and/or of the face, to head hair, the eyelashes, the eyebrows, body hair and/or the nails.

It may also comprise the usual cosmetic ingredients, such as for example oils, waxes, water, solvents, dyes, thickeners, surfactants, fillers, film-forming or non film-forming polymers.

Among the oils and/or the waxes, mention may be made of volatile or nonvolatile hydrocarbon and/or silicone and/or fluoro oils and waxes of animal, vegetable, mineral or synthetic origin.

Among the solvents, mention may be made of alcohols, especially $C_1$-$C_6$ alcohols such as ethanol or isopropanol; glycols such as ethylene glycol or propylene glycol; glycerol; propylene glycol ethers; ketones; esters; ethers; alkanes; cyclic aromatic compounds (toluene, benzene, xylene); aldehydes.

In a preferred embodiment, it may comprise at least one dye which may be a pigment or a water-soluble or liposoluble dye.

The pigments may be white or colored, mineral and/or organic, and micrometer-sized or nanometer sized pigments.

Among the mineral pigments and nanopigments, mention may be made of titanium, zirconium or cerium oxides, and of zinc, iron or chromium oxides, ferric blue, chromium hydrate and ultramarines (aluminosilicate polysulfides).

Among the organic pigments, mention may be made of carbon black and lacquers such as calcium, barium, aluminum, zirconium or strontium salts.

Among the water-soluble dyes, mention may be made of dyes that are common in the field in question such as the disodium salt of ponceau, the disodium salt of alizarine green, quinoline yellow, the trisodium salt of amaranth, the disodium salt of tartrazine, the monosodium salt of rhodamine, the disodium salt of fuchsin, and xanthophyll, and mixtures thereof. Mention may also be made of halo acid dyes, azodyes and anthraquinone dyes.

Moreover, the product may comprise the usual additives commonly employed in the field in question, such as antioxidants, perfumes, preserving agents, cosmetic active ingredients, vitamins, essential fatty acids, sphingolipids, self-tanning compounds such as DHA and sunscreens.

In a preferred embodiment, the product comprises at least one compound generally used for the temporary or permanent dyeing of head hair or of nails.

In another preferred embodiment, the treatment product may comprise at least one compound capable of temporarily dyeing the skin, such as self-tanning agents (especially DHA).

In another preferred embodiment, the treatment product may comprise at least one cosmetic active ingredient, especially a care active ingredient such as a moisturizer, an agent for whitening the skin, a care product for a pigmentation mark, a pro-desquamating agent, and an antiwrinkle agent.

The treatment product is intended to be applied to the skin of the face and of the body, to the mucus membranes and/or to the keratin fibers, such as the nails, the eyebrows or the head hair. It may be in any pharmaceutical form that can be envisioned, such as an oily or aqueous gel; a liquid or gelled emulsion, an oil-in-water, water-in-oil or multiple emulsion; a dispersion; a multiphase system, especially a biphase system; a solid composition such as a stick or bar.

This product may be in the form of a body hygiene composition; a hair composition, for example a hairstyling stick or hair makeup stick; a composition for making up the skin of the face, the body or the lips, for example a lipstick, liquid foundation in a stick or in a small dish, a face powder or an eyeshadow, a fixing base to be applied over a standard lipstick, a concealer stick, a lip gloss, eyeliner, mascara or temporary tattoo products; a care composition for facial or body skin including the scalp, the lips, the hair or the nails, for example a lip care balm or base, a daily care cream or a matting composition; an antisun or self-tanning composition.

In one embodiment of the invention, the camera 1, the applicator 7 and a screen are placed in a first location, and a data processing unit equipped with its peripherals is placed in a second location and is connected to the camera 1 and the applicator 7 by a communication network, for example of the Internet type. Interfaces such as modems will be connected to the camera 1 and the applicator 7, on the one hand, and to the data processing unit on the other hand. The data processing unit may be combined with a database which allows a larger choice of designs. Moreover, the data processing unit may be of high computing power. The data processing unit sends one or more images to the first location where the user selects an image and marks his approval. The control signal may then be produced at the first location by a local data processing means, or in the second location by said data processing unit on receiving a signal representative of the user's choice.

As a variant, the user can choose his image at a third location, for example at home on a personal computer connected to a communication network, mark his approval on an image, his approval then being transmitted to said data processing unit which then produces a signal intended to control the applicator, and sends it. The applicator, on receiving said signal, is ready to produce the image. The user then goes from the third location to the second location, for example a beauty salon, a manicure salon, a pharmacy, etc.

Alternatively, the user has the applicator at home. He may also have the camera at home. In this case, the image taken by the camera is sent to a remote data processing unit which performs the various necessary operations, proposes at least one image and produces and sends a signal intended to control the applicator on receiving the user's approval.

In one embodiment, a camera, a computer provided with a screen and a keyboard, and an applicator are placed in an acquisition and application zone, located for example at the user's home or in a beauty parlor. A computer and a database are placed in a remote zone, located for example at the home of the designer or at the home of a system operator. The computer and the database are connected by a computer link, preferably with a high data rate, while being able to be located at some distance one from the other. The computers are connected by a telecommunications network of the Internet type, preferably a fast Internet connection for example ADSL. The computer in the remote zone may have a high computing power, thereby benefiting the user, while the computer at the user's home or beauty parlor will be of the inexpensive mass-produced computer type.

Furthermore, a unit for formulating products is provided, for example in a laboratory, connected to the database by a computer link, preferably with a high data rate, while being able to be located at some distance one from the other.

In one direction, the data required by the camera in the acquisition and application zone will be sent to the computer located in the remote zone via the computer located in the acquisition zone, which may or may not carry out a first data processing. The data may serve to feed a database bringing together all the typologies of current or potential clients. The data contained in this base may then be used by a cosmetic product formulator in order to determine the characteristics of a product that it would be suitable to develop to meet the needs of this clientele.

In the other direction, a signal containing information intended for the applicator is carried. More specifically, the computer located in the remote zone processes data in order to generate an application message and/or data of one or more images calculated from the characteristics of the user. If the computer located in the acquisition zone receives the application message, it processes it, for example by decompression, if said message contains compressed data, and sends a control signal to the applicator. The said sending of the control signal may be subject to validation by the user.

If the computer in the acquisition zone receives data of an image, it displays said image on a screen. That computer may then require validation by the user. After said validation, the computer may send a request for an application message to the computer located in the remote zone.

In another embodiment, the camera and the computer are placed in an acquisition zone, located for example at the user's home. The applicator is placed in an application zone located for example in a beauty parlor. The applicator is connected to the computer by a link of the same type as that provided between the computer in the acquisition zone and the computer located in the remote zone.

In other words, the acquisition and application zones are distinct and may be distant. A personal code may be provided to identify characteristics specific to the user or characteristics chosen by the user and stored in the database. The personal code may be indicated to the user by the computer in the acquisition zone and will be requested from him by the computer in the application zone. The personal code may have the double function of identifying data of a user and of protecting the confidentiality of said data.

The invention claimed is:

1. A device for applying a cosmetic substance to at least a part of the human body comprising:
   a body part positioning device,
   an imaging device,
   a device that analyzes the topological and colorimetric characteristics and/or the surface state of said human body part based on elementary areas of the image,
   a device that obtains 3d coordinates of said part based on the image,
   a distance sensor,
   a cosmetic products applicator, and
   a positioning device that maintains a position of said cosmetic products applicator
   at a distance from said human body part ranging from 20 microns to 1 cm based on at least one signal generated by said distance sensor based on the distance between said cosmetic products applicator and said human body part.

2. A process for applying a cosmetic substance to at least a part of a human body comprising:
   imaging at least one human body part;
   determining a three dimensional coordinate of said human body part;
   analyzing at least one characteristic of a surface of said human body part;
   providing a cosmetic substance applicator;
   providing a positioning device that maintains a position of said cosmetic substance applicator at a controlled distance from said human body part, wherein said controlled distance varies from about 20 microns to about 5 centimeters; and,
   applying at least one cosmetic substance to said human body part with said cosmetic substance applicator.

3. The process according to claim 2, wherein said cosmetic substance is an agent selected from the group consisting of oils, inks, transfer prints, waxes, water, solvents, dyes, pigments, temporary self-tanning agents, thickeners, surfactants, fillers, film forming polymers, non film forming polymers, and mixtures thereof.

4. The process as claimed in claim 3, comprising steps of defining particular areas of said part and of applying agents successively over said particular areas.

5. The process as claimed in claim 3, comprising a step of storing, for a given person, the agents used and the local visual characteristics obtained.

6. The process as claimed in claim 3, in which the local characteristics obtained immediately after the application of the agents are monitored.

7. The process as claimed in claim 3, in which the application of agents is carried out by a head which follows a relief of said part.

8. The process as claimed in claim 7, in which the distance between the head and said part is monitored in real time.

9. The process as claimed in claim 8, in which the monitoring of the local characteristics obtained immediately after the application of the agents is carried out using the head.

10. The process as claimed in claim 2, in which said part is reconstructed three-dimensionally in order to obtain a three-dimensional representation.

11. The process as claimed in claim 2, in which the treatment agents are applied by airbrushing, by transfer printing, by tattooing or by a wipe impregnated with the agents to be applied.

12. The process according to claim 2, in which at least one digital image of said human body part to be treated is taken.

13. The process as claimed in claim 2, in which the image or images of said human body part to be treated is/are digitized.

14. The process as claimed in claim 2, in which the image taking and application steps are carried out in a first zone, and the analysis step is carried out in a second zone distinct from the first zone, with communication between said zones by means of a telecommunications network, of the Internet type.

15. The process as claimed in claim 2, in which the image taking step is carried out in a first zone, the analysis step is carried out in a second zone distinct from the first zone, and the application step is carried out in a third zone distinct from the first and second zones, with communication between said zones by means of a telecommunications network, of the Internet type.

16. A device for implementing the process according to claim 2 characterized in that it comprises a means of positioning said part, a means of taking images, a means of analyzing images in order to obtain the local characteristics of said part, and a means of applying makeup products over said part according to said local characteristics.

17. The device as claimed in claim 16, characterized in that the application means is supported by an arm which is articulated in order to be capable of following a relief of said part.

18. The device as claimed in claim 16, characterized in that the application means comprises at least one nozzle capable of spraying a treatment product, said head being of the piezoelectric, pneumatic, electrospray, thermospray or aerosol type.

19. The device as claimed in claim 16, characterized in that it comprises means for controlling the position of the application means with respect to the part of the area to be treated.

20. The device as claimed in claim 16, characterized in that it comprises means for automatically controlling the total amount and the partial amounts of each product according to the local visual characteristics desired.

21. A computer program comprising program code means to implement the steps of the process according to claim 2, wherein said program runs on a computer.

22. The process as claimed in claim 2, wherein said parts of the human body include hair, skin or nails.

23. The process according to claim 2, wherein said coloring agent or cosmetic treatment is formulated as temporary make-up in the physical form of creams, pastes, waxes, lacquers, solutions, dyes, pigments, emulsions, powders, and mixtures thereof.

24. The process for applying a cosmetic substance, according to claim 2, wherein said cosmetic treatment results in a non-therapeutic, temporary enhancement to the color, UV resistance, moisture content, gloss or texture of selected portions of the human body.

* * * * *